United States Patent
Song

(10) Patent No.: US 8,597,265 B2
(45) Date of Patent: Dec. 3, 2013

(54) VACUUM SEALING DRAINAGE DEVICE FOR BLEEDING WOUND TISSUE

(75) Inventor: Jiuhong Song, Wuhan (CN)

(73) Assignee: Wuhan VSD Medical Science & Technology Co., Ltd., Wuhan (CN)

( * ) Notice: Subject to any disclaimer, the term of this patent is extended or adjusted under 35 U.S.C. 154(b) by 422 days.

(21) Appl. No.: 12/840,314

(22) Filed: Jul. 21, 2010

(65) Prior Publication Data

US 2011/0071484 A1     Mar. 24, 2011

Related U.S. Application Data

(63) Continuation of application No. PCT/CN2009/074088, filed on Sep. 22, 2009.

(51) Int. Cl.
*A61M 1/00*     (2006.01)

(52) U.S. Cl.
USPC .......................................... 604/319; 604/313

(58) Field of Classification Search
USPC ........ 602/2, 42; 604/319, 540, 541, 543, 378, 604/266, 890.1, 313, 289, 290; 128/897
See application file for complete search history.

(56) References Cited

U.S. PATENT DOCUMENTS

| | | | |
|---|---|---|---|
| 6,866,657 B2 * | 3/2005 | Shchervinsky | 604/266 |
| 2005/0245903 A1 * | 11/2005 | Kuklin et al. | 604/890.1 |
| 2008/0208171 A1 * | 8/2008 | Argenta et al. | 604/540 |
| 2009/0270820 A1 * | 10/2009 | Johnson et al. | 604/290 |

\* cited by examiner

*Primary Examiner* — Jacqueline Stephens
*Assistant Examiner* — Benedict L Hanrahan
(74) *Attorney, Agent, or Firm* — Matthias Scholl P.C.; Matthias Scholl

(57) ABSTRACT

A vacuum sealing drainage device for a bleeding wound tissue, includes a multi-hole foam cushion (1) contacted with the bleeding wound tissue, a drainage pipe (2) with a side hole, a sealing film (3), a connector (4), a duct (17), a drainage container (5), and a vacuum source (6). The device further includes a glue film (7) and an leading-out pipe (8). The glue film (7) is disposed above the multi-hole foam cushion (1). An opening of the side hole of the drainage pipe (2) is contacted with the multi-hole foam cushion (1). The leading-out pipe (8) is connected to the drainage pipe (2), and is disposed above the glue film (7). The sealing film (3) is sealed on the glue film (7). The leading-out pipe (8) is received in the drainage container (5) via the duct (17), and the drainage container (5) is connected to the vacuum source (6) via the duct (17). The device increases time of maintaining elasticity and a humid environment for the multi-hole foam cushion, which is helpful for wound healing. The sealing and drainage thereof are convenient and reliable.

14 Claims, 9 Drawing Sheets

VACUUM SEALING DRAINAGE DEVICE FOR BLEEDING WOUND TISSUE

CROSS-REFERENCE TO RELATED APPLICATIONS

This application is a continuation of International Patent Application No. PCT/CN2009/074088 with an international filing date of Sep. 22, 2009, designating the United States, now pending. The contents of all of the aforementioned applications, including any intervening amendments thereto, are incorporated herein by reference.

BACKGROUND OF THE INVENTION

1. Field of the Invention

The invention relates to a vacuum sealing drainage device for a bleeding wound tissue, and more particularly to a treating device that is designed for treatment of injury areas of various body surface tissues and performs vacuum sealing drainage treatment on a wound surface caused by injury, burn, infection, compression, endocrine dyscrasia, vascular occlusion, radioisotope exposure, surgeries, surgical complications, insect and snake bite, cryogenic burns, and so on.

2. Description of the Related Art

A vacuum sealing drainage technology (VSD for short) is invented by Dr. Wim Fleischman from ULM University of Germany in 1992 and theory thereof has been formed, and it is for drainage of wound surface of limbs. In 1994, Chinese professor Qiu Huade first applied the VSD technology to general surgical departments, and initiated application of the VSD technology in the general surgical departments. Professors Wang Yanfeng and Qiu Huade got the first patent of the VSD technology with a patent number CN 2276350 on Mar. 18, 1998.

A basic configuration of the conventional VSD technology comprises a vacuum source (comprising a medical suction unit, a central vacuum unit, or a vacuum drainage bottle), a drainage pipe, polyvinyl alcohol foams, other medical multi-hole foams, sponges or gauzes (a multi-hole foam cushion for short), a breathable film for adhesion and sealing (a sealing film for short), a connector (comprising a two-way connector, a three-way connector, or multi-way connector), and a drainage container. A structure thereof is: a drainage with a side hole on one end (normally two pipes parallel to each other, one pipe for a small multi-hole foam cushion, and three or more pipes parallel to each other for a comparatively big one) is inserted in the multi-hole foam cushion with a hole. As multiple multi-hole foam cushions are used, outlets of the drainage pipe are combined into one outlet via the three-way connector, the two-way connector, or the multi-way connector, then the vacuum source is connected for drainage, whereby conducting liquefaction materials such as exudation, cataclysm, liquefaction necrosis tissue fragments, pus and so on into the drainage container.

In use, the drainage pipe with multiple side holes is wrapped with the multi-hole foam cushion, and disposed on the wound surface or a wound cavity, a sealing film is used to tightly seal the multi-hole foam cushion and an outlets of the drainage pipe whereby separating them from the outside, the drainage container is connected, and finally the vacuum source is connected (or a vacuum drainage bottom made by combing the drainage container with the vacuum source), and thus a high-efficient drainage system (VSD system) is formed. In this system, negative pressure is transferred to the multi-hole foam cushion via rigid transmission of the drainage pipe, and is distributed on every point on the multi-hole foam cushion along a trend of the drainage pipe. Since vesicles in the multi-hole foam cushion are connected to each other and are rich in flexibility, negative pressure can reach every point of a targeted drainage area whereby forming omnibearing drainage. Under the action of the negative pressure, comparatively big, tender and blocky educts are cut and molded into granules, which enter the drainage pipe via openings of the multi-hole foam cushion or vesicles connected to each other, and then are quickly inhaled into the drainage container. Big educts that may block the drainage pipe are stopped by the multi-hole foam cushion, adhered to the surface of the multi-hole foam cushion, and can only leave a body of the device along with the multi-hole foam cushion as drain is removed or replaced. Closing of the sealing film maintains negative pressure operating as drainage force, and the drainage area is separated from the outside, which effectively prevent pollution and cross infection. Since negative pressure is uniformly distributed on the surface of the drainage area via the soft multi-hole foam cushion operating as a medium, and capable of effectively preventing complications, such as ischemia, necrosis, perforation and so on, caused by suction of organs or tissues as one drainage pipe is used for vacuum drainage.

Compared with normal dressing change, the VSD technology is capable of timely removing exudates and necrotic tissues in the drainage area, and thus the drainage area can enter a "zero accumulation" state, and the wound surface can quickly obtains a clean environment, and greatly reduce heavy absorption of toxins by the body. Even if a comparatively big cavity gap exists, the cavity gap is quickly reduced due to existence of the negative pressure. For superficial wound surface, the sealing film and the multi-hole foam cushion cause a local environment to be more close to a physiological humid state. Negative pressure stimulation on soft tissues of the wound surface is helpful for improvement of a local microenvironment and subsidence of a tissue swelling, accelerates regeneration of granulation tissues in the wound surface, decreases healing time of the wound surface, requires no dressing change within 3-7 days of VSD treatment, reduces workload of medics, alleviates pain of patients, and reduces overall medical cost.

In China, the VSD technology is widely applied to fields such as traumatology departments, orthopedics departments, general surgery departments, burn departments, and so on.

However, during use of the conventional VSD technology in drainage of a bleeding wound tissue, several problems exist: 1) sealing thereof is inconvenient: good sealing is a key for ensuring drainage effect, and the most difficult step during the whole vacuum sealing drainage. Common-used sealing methods comprise: a stabbing hole method, a mesentery method, a suture method, a dumpling method, and so on. However, the above-mentioned methods are very complex during practical operation, and operative doctors can grasp them after repeated operation and practice. In addition, infirm sealing often causes air leakage, and further decreasing of treatment effect or even failure of the VSD system. 2) a leading-out end of the drainage pipe is used as an outlet for negative-pressure conduction and drainage, there are few directions of the outlet for the negative-pressure conduction and the drainage, and the negative-pressure conduction and the drainage often occur in a single horizontal or a vertical direction, which easily cause non-uniform negative pressure conduction and pipe blockage. Moreover, as pipe blockage occurs, washing is inconvenient. Conventional washing methods comprise: 1. setting another rubber pipe on the wound surface, and using a mesentery method to seal a leading-out position of the rubber pipe, which increase possibility of "air leakage" and difficulty of sealing; 2. inversely injecting washing flushing liquid from an original drainage pipe may re-inject drainage exudates on the wound surface and cause "reverse infection"; 3. stabbing a hole on and injecting flushing liquid in the multi-hole foam cushion, but the sealing film needs to be adhered to the hole on the multi-hole foam cushion, which increases operation difficulty. 3) it is inconvenient for drainage of massive and irregular wound surface. A leading-out end of the drainage pipe is connected via a connector, and a large amount of connectors are used to combine outlets of the drainage pipe into one outlet. And thus an intersected mesh structure like a branch is formed, which makes movement of a patient very inconvenient. 4) in clinical use, the sealing film is used to seal the multi-hole foam cushion with healthy skin, since follicles in the healthy skin need normal permeable and breathable metabolism, permeability of the sealing film should be as large as possible, otherwise phenomenon such as skin rash, folliculitis, blushing caused by water immersion and so on may occur on the healthy skin, which causes a patient to consciously or unconsciously scratch and rub the sealing film due to troublesome symptoms such as itching and so on, stickiness of the sealing film to disappear and to detach from the skin surface, and further air to enter a sealing area resulting in decreasing of effect or complete failure of vacuum sealing drainage since water immerses between the skin and the sealing film. The multi-hole foam cushion requires complete sealing and permeability of the sealing film be as small as possible, otherwise water loss will occur on the multi-hole foam cushion due to long-term and small airflow that causes the multi-hole foam cushion to become dry, and finally the multi-hole foam cushion loses elasticity and a humid environment, and healing time of the wound surface is increased. Thus a contradiction between two opposite reaction principles is formed. The conventional sealing film cannot simultaneously meet requirements for normally permeable, breathable, and metabolism skin, and for firm sealing of the multi-hole foam cushion. 5) for a massive wound surface, as two or more multi-hole foam cushions are needed, normally a drainage pipe with a side hole in the cushion is pulled out, and an operative doctor cuts more side holes on the drainage pipe, extends a length of the drainage with the side holes, and joints, serially connects, or parallel connects the multi-hole foam cushions, which is very troublesome.

Therefore, it is an urgent and important task to improve use of the conventional VSD technology in healing a bleeding wound tissue.

SUMMARY OF THE INVENTION

It is an objective of the invention to provide a vacuum sealing drainage device for a bleeding wound tissue that is capable of addressing the above-mentioned problems with the conventional vacuum sealing drainage device.

The invention is implemented as follows: A closed negative pressure drainage device for a bleeding wound tissue, comprising a multi-hole foam cushion contacted with the bleeding wound tissue, a drainage pipe with a side hole, a sealing film, a connector, a duct, a drainage container, a vacuum source, it further comprises a glue film and an leading-out pipe, the glue film is disposed above the multi-hole foam cushion, an opening of the side hole of the drainage pipe is contacted with the multi-hole foam cushion, the leading-out pipe is connected to the drainage pipe, and disposed above the glue film, the sealing film is sealed on the glue film, the leading-out pipe is received in the drainage container via the duct, and the drainage container is connected to the vacuum source via the duct.

In the invention, the drainage pipe is disposed between the multi-hole foam cushion and the glue film.

In the invention, the drainage pipe is circular or flat, and is disposed at the top of the glue film and integrally formed with the glue film.

In the invention, a flow meter is connected to the duct between the leading-out pipe and the drainage container.

In the invention, the drainage pipe and the glue film are integrally formed.

In the invention, a support is disposed in the multi-hole foam cushion, one end of the support is disposed in the multi-hole foam cushion, and the other end of the support is fixed on the drainage pipe and/or on the glue film.

In the invention, a pressure sensor is connected to the duct, the pressure sensor is connected to a CPU, and the CPU is connected to the vacuum source.

In the invention, the sealing film is disposed around the glue film.

In the invention, the drainage pipe is one pipe.

In the invention, the drainage pipes are two to five pipes disposed parallel to each other.

In the invention, the drainage pipes are at least two pipes crossingly connected to each other and integrally formed.

In the invention, multiple burrs are disposed on the support.

In the invention, a bacterial filter and an odor filter are disposed between the drainage container and the vacuum source.

In the invention, the drainage pipe is #-shaped (number-sign shaped), +-shaped (plus sign-shaped), 工-shaped (H-shaped), or ✳-shaped (star-shaped).

In the invention, the support is hollow, the support is connected to the drainage pipe, and an opening is disposed on the support.

In the invention, one to five leading-out pipes are connected to the drainage pipe, and the leading-out pipes and the drainage pipe are integrally formed.

In the invention, a lower end surface of the support is a concave contour.

In the invention, a sealing cover is disposed on the leading-out pipe.

In the invention, a sealable sample connection is disposed on the leading-out pipe.

Advantages of the vacuum sealing drainage device for a bleeding wound tissue of the invention comprise: 1) wound surface is sealed via the glue film on the multi-hole foam cushion (the glue film features very low air permeability, and can be made by other materials and features very low air permeability), which greatly increases time of maintaining elasticity and a humid environment for the multi-hole foam cushion, and is helpful for healing of the wound surface. 2) only surrounding of the glue film is sealed with the sealing film (or the glue film and surrounding thereof are covered with the sealing film), and the leading-out end of the drainage pipe is not sealed, which reduce possibility of air leakage of the VSD system, and make sealing of the vacuum sealing drainage simple and reliable; moreover, the sealing film has very high permeability, good compatibility with skin, and low sensitization rate, and is helpful for normal metabolism of healthy skin around the wound surface. 3) the leading-out pipe is connected to every drainage pipe, there are multiple directions for the outlets, an outlet for each drainage pipe can operate as a drainage port, and as a flush port as pipe blockage occurs, which makes drainage and flushing very convenient; meanwhile, a fixed leading-out pipe is allocated for flushing during operation, and thus preventing reverse infection as one leading-out pipe is used for drainage and flushing. Side pipes led out from the drainage pipe can operate as a sampling channel for drainage. 4) the drainage method of transmitting negative pressure or drainage are more uniform and reasonable than side drainage, and pipe blockage does not easily occurs, especially as the leading-out pipe is disposed at intersection of the drainage pipe. 5) for mass and irregular wound surface, the leading-out pipe is received in the drainage container via a multi-way connector, which makes drainage very convenient, prevents a branch-shaped mesh (as shown in FIG. 14), and makes it convenient for movement of a patient. 6) operation time is reduced, pain of a patient is alleviated, and healing time of the wound surface of the patient is decreased.

Figure 1:
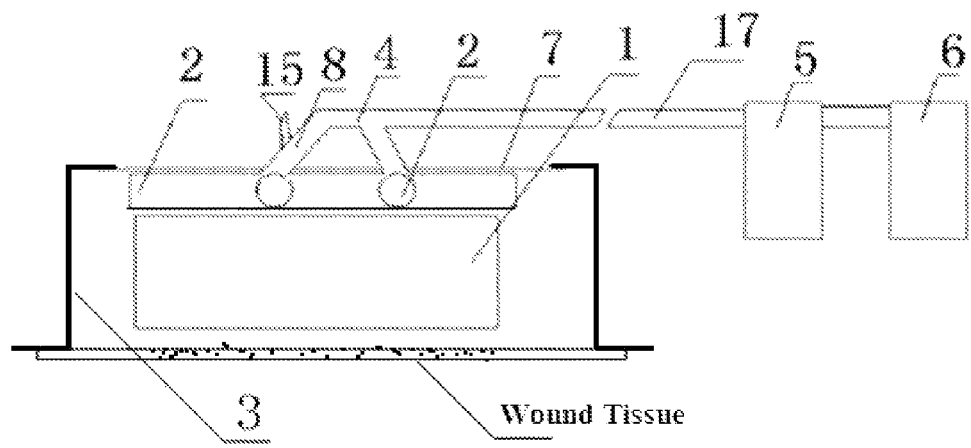
FIG. 1 is a schematic view of a vacuum sealing drainage device for a bleeding wound tissue of a first embodiment of the invention.

In the drawings, the following reference numbers are used: 1—multi-hole foam cushion; 2—drainage pipe; 3—sealing film; 4—connector; 5—drainage container; 6—vacuum source; 7—glue film; 8—leading-out pipe; 9—support; 10—burr; 11—sealing cover; 12—groove; 13—opening; 14—concave contour; 15—sampling port; 16—flow meter; 17—duct; 18—bacterial filter; 19—odor filter; 20—pressure sensor; 21—CPU

DETAILED DESCRIPTION OF THE EMBODIMENTS

Further description of the invention will be given below in conjunction with accompanying drawings, and they are not to be construed as limitation to the invention and are illustrative only. Merits of the invention will be more readily and understandable from the following detailed description.

As shown in the drawings, a closed negative pressure drainage device for a bleeding wound tissue, of the invention comprises a multi-hole foam cushion 1 contacted with the bleeding wound tissue, a drainage pipe 2 with a side hole, a sealing film 3, a connector 4, a drainage container 5, and a vacuum source 6, and further comprises a glue film 7 and an leading-out pipe 8. The glue film 7 is disposed above the multi-hole foam cushion 1, an opening of the side hole of the drainage pipe 2 is contacted with the multi-hole foam cushion 1, the leading-out pipe 8 is connected to the drainage pipe 2, and disposed above the glue film 7, the sealing film 3 is sealed on the glue film 7, the leading-out pipe 8 is received in the drainage container 5, and the drainage container 5 is connected to the vacuum source 6.

The above-mentioned drainage method makes drainage extend in all directions, transmitting negative pressure or drainage are more uniform and reasonable than side drainage (an original drainage device drainage or transmits negative pressure at a leading-out end of the drainage pipe), and pipe blockage does not easily occurs, especially as the leading-out pipe is disposed at intersection of the drainage pipe (as shown in FIGS. 1-4).

The drainage pipe 2 is disposed between the multi-hole foam cushion 1 and the glue film 7, the drainage pipe 2 and the glue film 7 are integrally formed (or the drainage pipe is not connected to the glue film). The groove 12 can be disposed on the multi-hole foam cushion, and the drainage pipe is disposed in a groove in the multi-hole foam cushion.

Figure 3:
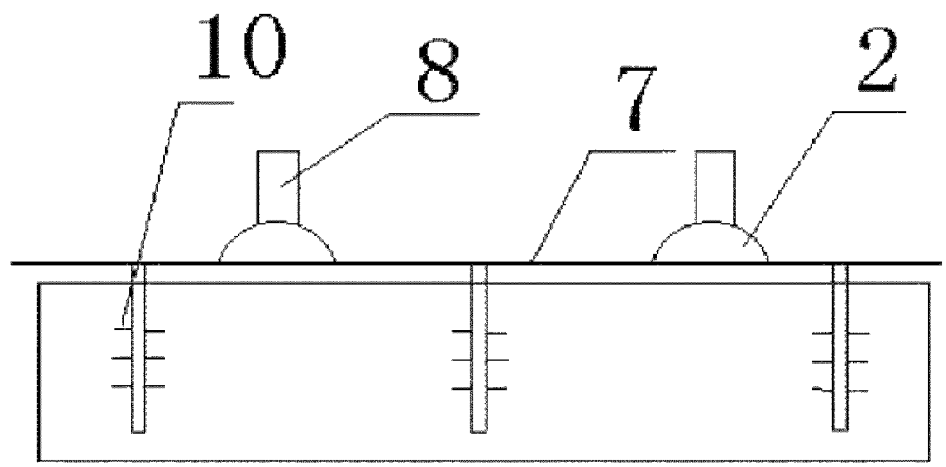
FIG. 3 illustrates a position relationship among a leading-out pipe, a drainage pipe, a glue pipe, and a support of the invention.

The drainage pipe 2 is circular or flat (or employs other structure), and is disposed at the top of the glue film 7 and integrally formed with the glue film 7 (as shown in FIG. 3).

The support 9 is hollow, the support 9 is connected to the drainage pipe 2, and an opening 13 is disposed on the support 9 (so as to assist in drainage). Lower end surface of the support 9 (made of extensible soft materials) is concave contour (compared with lower end surface of the support being a plane, it increases contact area with the wound surface and reduces pressure on wound tissues in a vacuum state).

Figure 2:
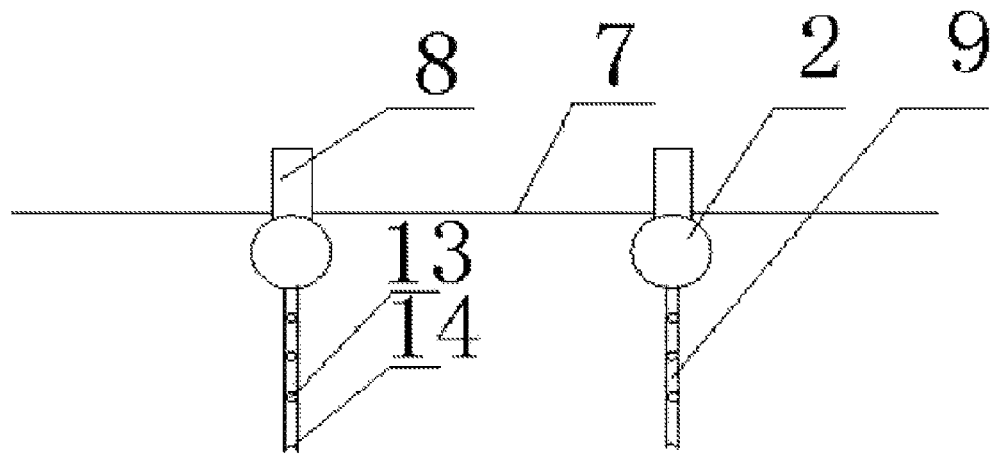
FIG. 2 illustrates a position relationship among a multi-hole foam cushion, a sealing film, and a glue film of the invention (in which a dashed part is an invisible part)
Figure 4:
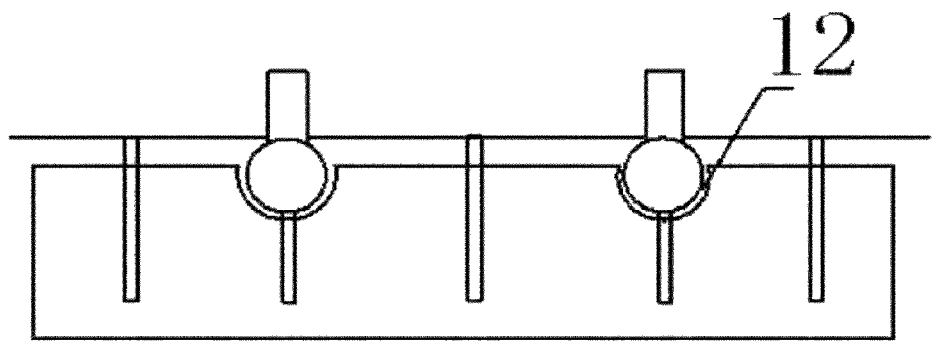
FIG. 4 illustrates a position relationship among a leading-out pipe, a drainage pipe, a glue pipe, a support, and a multi-hole foam cushion of the invention.
Figure 5:
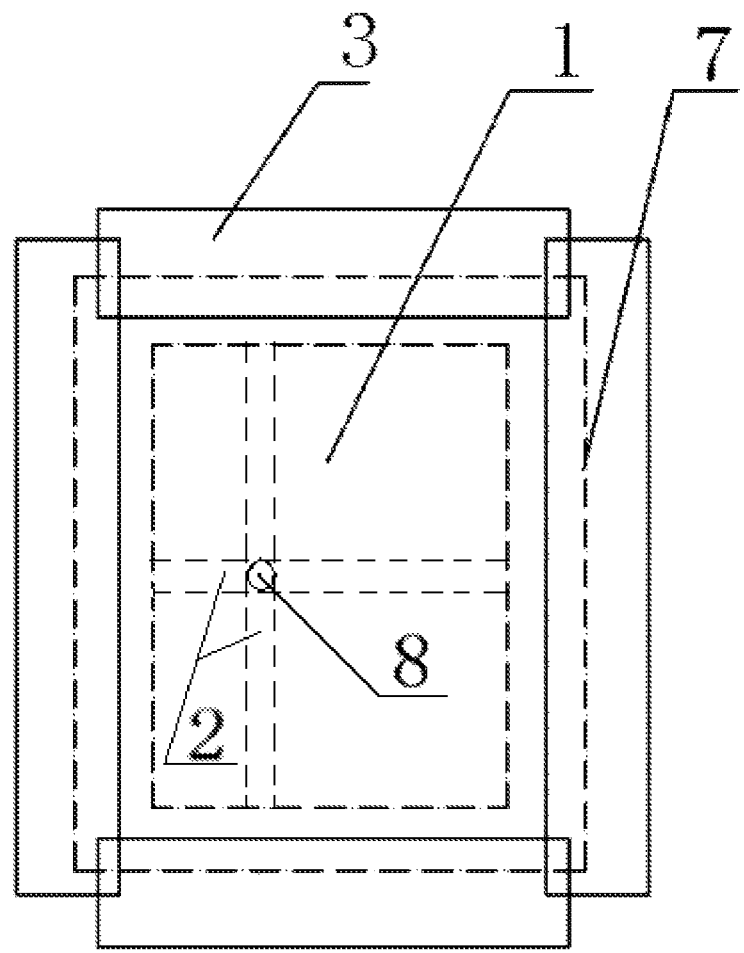
FIG. 5 illustrates another position relationship among a leading-out pipe, a drainage pipe, a glue pipe, a support, and a multi-hole foam cushion of the invention.

A support 9 is disposed in the multi-hole foam cushion 1, one end of the support 9 is disposed in the multi-hole foam cushion 1, and the other end of the support 9 is fixed on the drainage pipe 2 and/or on the glue film 7. Multiple burrs 10 are disposed on the support 9 (as shown in FIGS. 2-4). The structure has the following advantages: firstly, the support enables the multi-hole foam cushion to support between the bleeding wound tissue and the sealing film, and hole gaps and vesicles in the multi-hole foam cushion to maintain a normal state or to deform slightly, and conducts liquefaction materials such as exudation, cataclysm, liquefaction necrosis tissue fragments, pus and so on into the drainage pipe via the vesicles connected to each other whereby reducing possibility of failure of drainage due to pipe blockage. Secondly, the support enables the multi-hole foam cushion to keep elasticity of a vacuum environment in a normal state, reduces tightly contact between the multi-hole foam cushion and the bleeding wound tissue due to negative pressure, prevents unwanted adhesion between the multi-hole foam cushion and growing parts of cells of the bleeding wound tissue, is helpful for growth of granulation of the bleeding wound tissue, and decreases healing time of the bleeding wound tissue. Meanwhile, the burr rivets and fixes the drainage pipe, the support, the glue film, and the multi-hole foam cushion into a whole, and the support is not easily to be pulled from the multi-hole foam cushion.

The sealing film 3 is disposed around the glue film 7, the method only needs posting films to surrounding of the glue film and is very simple. Using the method, a mesentery method for sealing the drainage pipe at an outlet of the drainage pipe is not required in film sealing and posting, which makes sealing more convenient.

Figure 7:
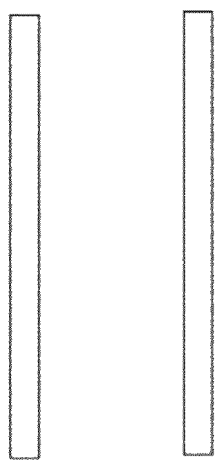
FIG. 7 is a schematic view of a pair of pipes parallel to each other.
Figure 8:
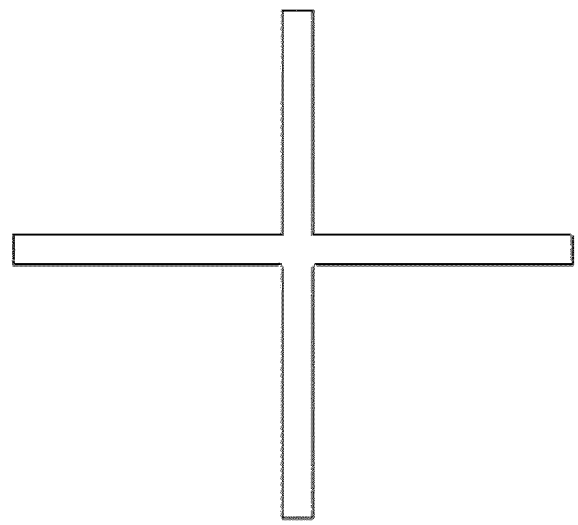
FIG. 8 is a schematic view of a +-shaped drainage pipe of the invention.
Figure 9:
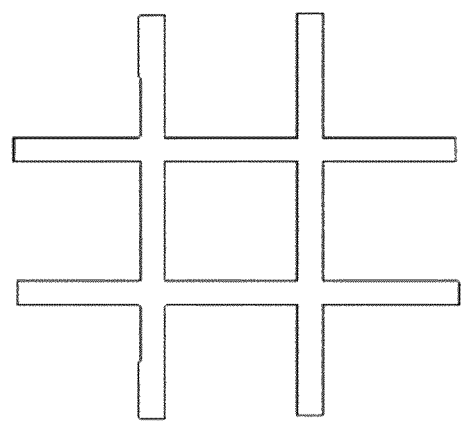
FIG. 9 is a schematic view of a #-shaped drainage pipe of the invention.
Figure 10:
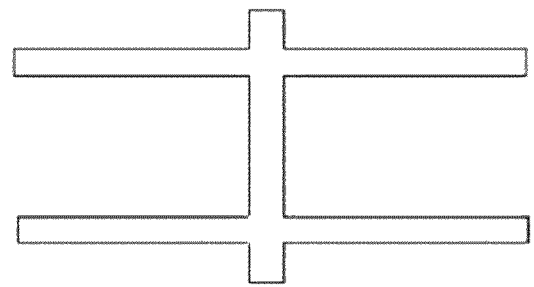
FIG. 10 is a schematic view of a 工-shaped drainage pipe of the invention.
Figure 11:
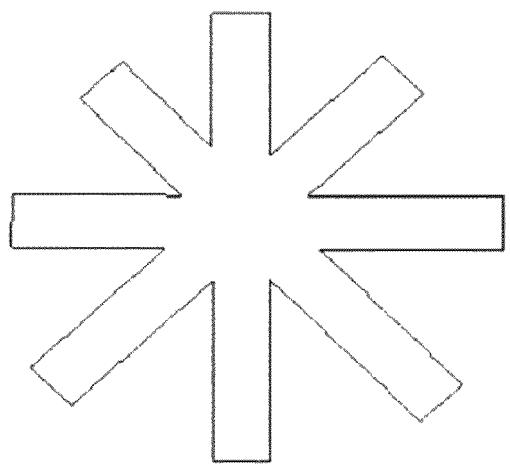
FIG. 11 is a schematic view of a ⁂-shaped drainage pipe of the invention.

The drainage pipe 2 is one pipe, or the drainage pipes 2 are two to five pipes disposed parallel to each other. As the drainage pipe is one pipe, the structure is applicable to small wound surface. As the drainage pipes 2 are two to five pipes disposed parallel to each other. (normally two pipes, and three or more drainage pipes for a comparatively large area), the structure is applicable to regular wound surface (as shown in FIG. 7).

The drainage pipes are at least two pipes crossingly connected to each other and integrally formed. For example, the drainage pipe 2 is #-shaped, +-shaped, ⊥-shaped, or other intersected structure. The structure makes drainage extend in all directions. Moreover, negative pressure transmission is more uniform and helpful for negative pressure transmission and drainage (as shown in FIGS. 8-11).

One to five leading-out pipes 8 are connected to the drainage pipe 2, and the leading-out pipes 8 and the drainage pipe 2 are integrally formed.

Figure 6:
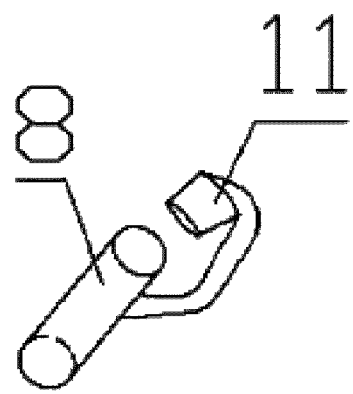
FIG. 6 is a schematic view of a leading-out pipe and a sealing cover of the invention.

A sealing cover 11 is disposed on the leading-out pipe 8, and the structure prevents air pollution as the leading-out pipe does not drain, or flushes (as shown in FIG. 6).

Figure 12:
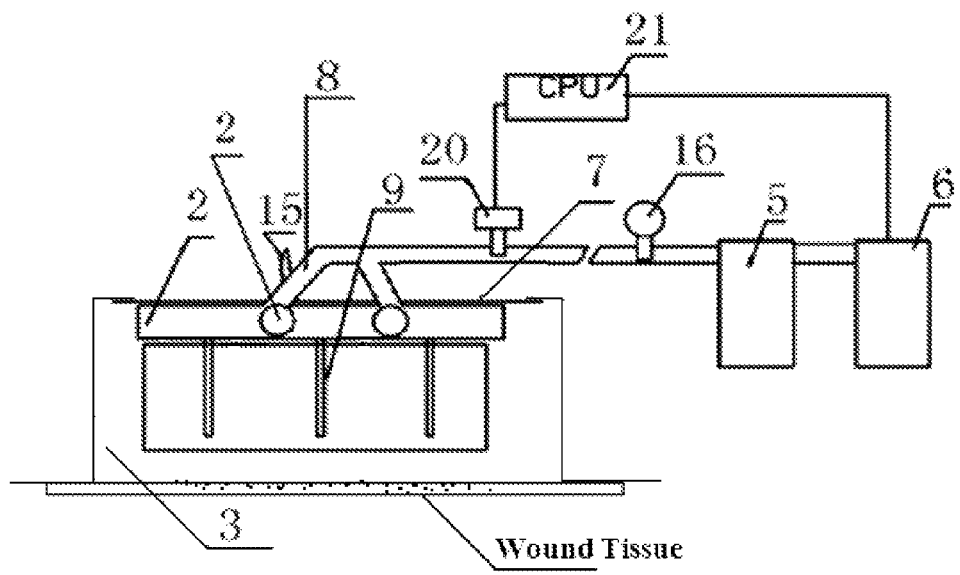
FIG. 12 is a schematic view of a vacuum sealing drainage device for a bleeding wound tissue of a second embodiment of the invention.

A flow meter 16 is connected to the duct 17 between the leading-out pipe 8 and the drainage container 5 (as shown in FIG. 12). Functions of the flow meter comprise: first, monitoring active bleeding of wound surface whereby preventing hypovolemic shock; second, monitoring mass loss of humor whereby preventing hypoproteinemia caused by mss loss of mass albumen; third, providing data support for fluid replacement and supplementing colloid; fourth, compared with a drainage bottom with graduation that records loss of humor, the flow meter operates to record loss of humor within unit time, and provides timely data support for clinical emergency treatment.

A sealable sampling port 15 is disposed on the leading-out pipe 8, which overcomes a problem with the conventional VSD device that no sampling port is disposed therein. During sampling of the conventional VSD device, a connection position of the drainage pipe needs to be opened for sampling, and the sampling process causes a possibility of new polluted wound surface. However, a special sampling port prevents occurrence of the problem. The sampling port has the following functions: first, performing qualitative analysis on composition of drainage liquid and providing basis for clinical treatment; second, performing drug sensitive test on samples of drainage whereby providing optimum antibiotics and anti-bacterial and anti-infection treatment (as shown in FIG. 1 and FIG. 12).

Figure 13:
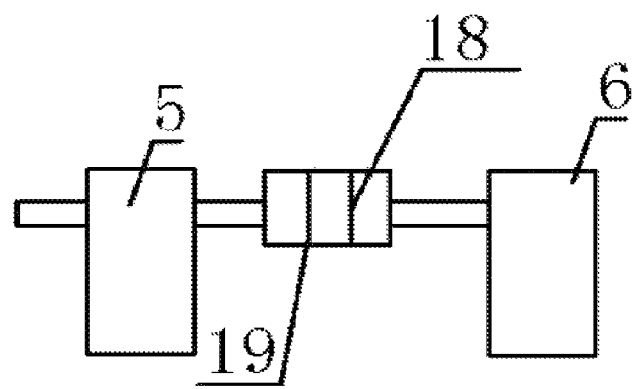
FIG. 13 illustrates connection of a filter, a drainage container, and a vacuum source.
Figure 14:
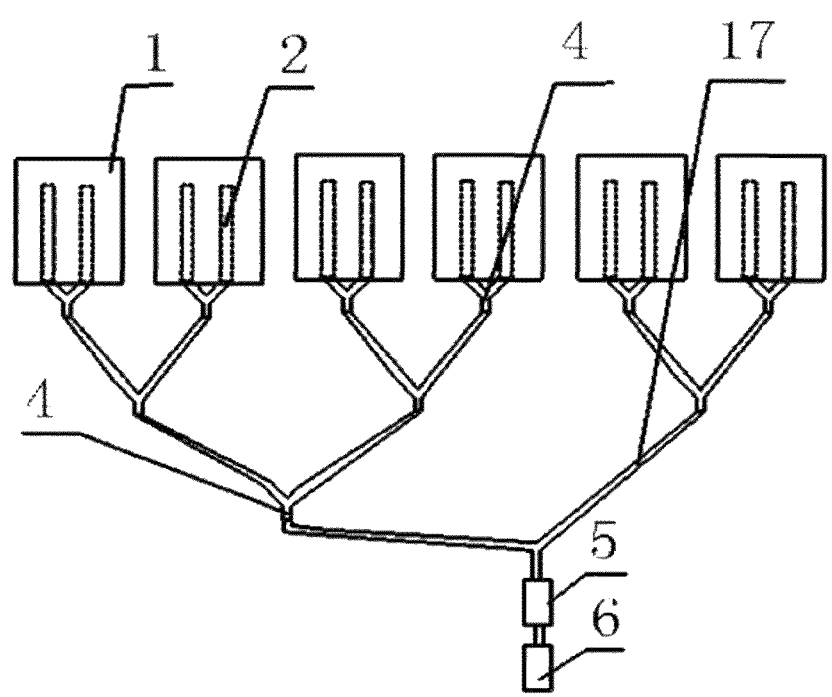
FIG. 14 is a schematic view of a branch-shaped mesh formed via a conventional vacuum sealing drainage.
Figure 15:
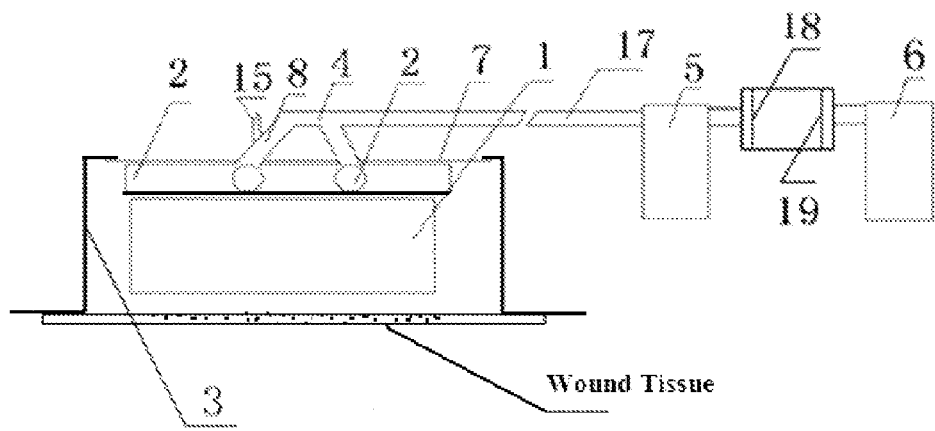
FIG. 15 is a schematic view of a vacuum sealing drainage device for a bleeding wound tissue comprising a bacterial filter and an odor filter of a third embodiment of the invention.
Figure 16:
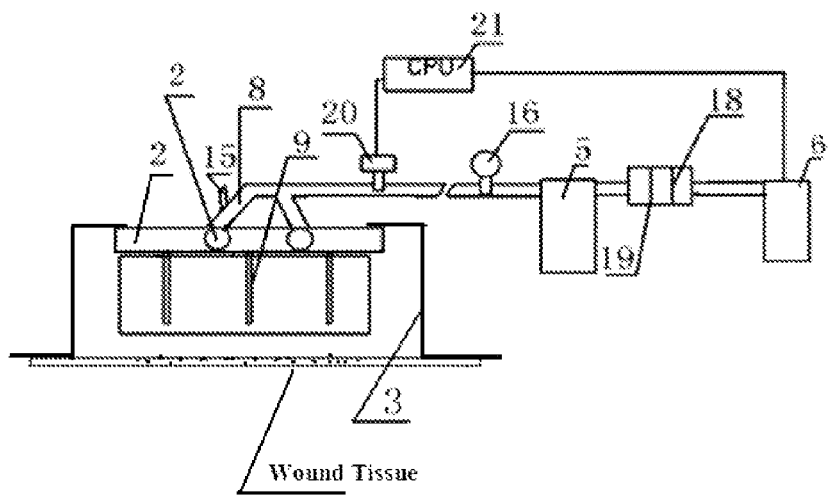
FIG. 16 is a schematic view of a vacuum sealing drainage device for a bleeding wound tissue comprising a bacterial filter and an odor filter of a fourth embodiment of the invention.

A bacterial filter 18 and an odor filter 19 are disposed between the drainage container 5 and the vacuum source 6. The bacterial filter is capable of reducing bacteria, especially anaerobic bacteria, that enter the next drainage channel, such as a central vacuum source, whereby preventing a possibility of pollution of a central vacuum system in a hospital. The odor filter is capable of reducing foul odor generated on the wound surface that overflows from the system (as shown in FIG. 13).

A pressure sensor 20 is connected to the duct 17, a CPU 21 is connected to the pressure sensor 20, and the CPU 21 is connected to the vacuum source 6. The pressure sensor controls opening and closing of the vacuum source, or adjusts negative pressure output from the vacuum source by measuring pressure transmitted in the multi-hole foam cushion in the duct and processing a pressure signal by the CPU, and via commands from the CPU. The negative pressure is transmitted to the multi-hole foam cushion by drainage capability and the drainage pipe, whereby adjusting pressure between the vesicle and the hole gap in the multi-hole foam cushion.

In use, the support is inserted into the multi-hole foam cushion, the glue film and the drainage pipe are disposed on the multi-hole foam cushion, surrounding of the glue film is sealed via the sealing film, the duct is connected to the leading-out pipe on the glue film, and the drainage container and the vacuum source are connected, and thus they can be used. During use, a multi-way connector is connected on the leading-out pipe. If there are four leading-out pipes, a five-way connector can be used, and thus the duct is connected to the drainage container, or only two leading-out pipes are used as outlets, and other leading-out pipes are used during flushing.

Advantages of the VSD device of the invention is described below via comparison between clinical cases of the VSD device of the invention and those of the conventional VSD device.

The conventional VSD device is two parallel drainage pipes disposed in the multi-hole foam cushion, sealed via the sealing film, and connected to the drainage container and the vacuum source via the connector and the duct.

The VSD device of the invention is, a flat #-shaped drainage pipe is disposed at the top of the glue film, the support is disposed at the bottom of the glue film, a burr is disposed on the support, the support is received in the multi-hole foam cushion, the leading-out pipe is disposed on the drainage pipe, the sampling port is disposed on the leading-out pipe, and connected to the drainage container via the duct, and to the vacuum source. The bacterial filter and the odor filter are disposed between the drainage container and the vacuum source. The multi-way connector is connected to the drainage container via the duct, and a leading-out pipe is left as a flushing port. Surrounding of the glue film is sealed via the glue film.

Patients having soft tissue avulsion injury, open fracture and soft tissue defect count up to 180, duration of each thereof is 3 months, and are divided into an even group and an odd group according to sequence of treatment. The odd group with 90 patients is treated with the conventional VSD device (Group A), and the even group with 90 patients is treated with the VSD device of the invention (Group B), observation time is a course of VSD treatment, namely 5-7 days. In the above-mentioned course of treatment, comparison is performed in terms of sealing operation time, a pipe blockage rate, a dry rate of the multi-hole foam cushion, and percentage of dents on the wound surface. Time of producing one product is listed in the following tables:

TABLE 1 comparison between the VSD device of the invention and
the conventional VSD device during and after clinical operation.

| | Compared item (taking 450 cm² for example) | |
|---|---|---|
| | Conventional VSD device (Group A) | VSD device of the invention (Group B) |
| Sealing operation time during operation | 10-20 minutes | 3-5 minutes |
| Pipe blockage rate | Above 60% | Below 10% |
| Dry rate of multi-hole foam cushion | Above 70% | Below 10% |
| percentage of dents on the wound surface | Above 50% | Below 10% |
| Time of producing one product | 3-4 minutes | Within 1 minute |

Compared items are: area of the wound surface is approximately 450 cm². Time of producing one product for the conventional VSD device refers to time of inserting the drainage pipe in the multi-hole foam cushion, and that for the invention refers to time of combining the glue film, the drainage pipe, and the leading-out pipe with the multi-hole foam cushion.

Clinical comparison and analysis between the VSD device of the invention and the conventional VSD device after operation are described below.

From January 2009 to September 2009, the inventor compares 30 patients having soft tissue defect and concurrent infection respectively treated via the conventional VSD device and the VSD device of the invention. All the patients are treated two weeks after injuring, and this belongs to post processing, an area of the wound surface is above 100 cm² and deep into a muscular layer, and all of them have tissue necrosis. The two groups all exclude patients having wound surface on face, hands, feet, and perineal floor, chronic soft tissue infection, concurrent osteomyelitis, age above 50, and concurrent diabetes. A conventional VSD device comprise 17 man and 13 woman having ages between 6 and 48, an average age of 27.8, an average area of wound surface of 182.3 cm². Patients using the VSD device of the invention comprise 16 man and 14 woman having ages between 7 and 49, an average age of 28.3, an average area of wound surface of 169.8 cm². Physical conditions and wound surface of the two groups are approximately the same, and thus having comparability, and can be tested and processed by statistics.

Tables 2-1 and 2-2 illustrate injury conditions, injury parts, and repairing methods. Table 2-3 lists cleaning time of wound surface of the two groups. Cleaning time of wound surface refers to time from treatment to closing of wound surface of soft tissue defect and infection, Standards of cleaning of the wound surface and closing thereof are: the wound surface is flat and clean, no necrotic tissues or exudates occurs; edema of the wound surface disappears; granulation tissue of the wound surface is fresh and in the shape of a pink granule, and easily bleeds once being contacted; the wound surface ensures successful secondary suture, skin grafting, and skin flap transfer. Time is calculated in days from finding wound surface infection or debridement, and removing necrotic tissue, to one day before repairing wound.

TABLE 2-1

Injuring reason and complications

| | injuring reason | | | complications | | |
|---|---|---|---|---|---|---|
| Group | Traffic accident | Machine | Pressing of heavy object | Bone exposure | Fracture | multiple trauma |
| Conventional VSD group | 18 | 10 | 2 | 21 | 8 | 19 |
| VSD group of the invention | 15 | 11 | 4 | 19 | 10 | 20 |

TABLE 2-2

Injury parts and repairing methods

| | Wound parts | | Repairing methods of wound surface | | |
|---|---|---|---|---|---|
| Group | Limb | Body | secondary suture + skin grafting | skin grafting | Skin flap transfer |
| Conventional VSD group | 26 | 4 | 5 | 22 | 3 |
| VSD group of the invention | 25 | 5 | 4 | 25 | 1 |

TABLE 2-3

Time distribution of cleaning of wound surface

| | Time (day) | | | | | | |
|---|---|---|---|---|---|---|---|
| | 0~6 | 7~13 | 14~20 | 21~27 | 28~34 | 35~41 | Sum |
| Conventional VSD group | 8 | 14 | 4 | 3 | 1 | 0 | 30 |

TABLE 2-3-continued

Time distribution of cleaning of wound surface

| | Time (day) | | | | | | |
|---|---|---|---|---|---|---|---|
| | 0–~6 | 7~13 | 14~20 | 21~27 | 28~34 | 35~41 | Sum |
| VSD group of the invention | 13 | 10 | 5 | 2 | 0 | 0 | 30 |

Cleaning time of the wound surface of the conventional VSD group is 5-15 days, the wound surface is reduced at different degrees, 22 patients undergo skin grafting, and 3 patients undergo skin flap transfer. Cleaning time of the wound surface of the VSD group of the invention is 3-10 days, and is significantly decreased in comparison with the conventional VSD group (P<0.01, there is significant difference therebetween), decreasing in the wound surface of the VSD group of the invention is more obvious, 25 patients undergo skin grafting, and 1 patient undergo skin flap transfer.

The above results indicate treatment effect of using the VSD device of the invention to handle soft tissue defect and concurrent infection is better than the conventional VSD device.

Table 1, Table 2-1, Table 2-2, and Table 2-3 indicate the VSD device of the invention is better than domestic and oversea products and various related technical documents and bibliographies in terms of ease of clinical operation, understanding and application of principles, reasonable arrangement of structure and so on. Merits or advantages are beyond imagination of those skilled in the art.

It should noted that it will be obvious to those skilled in the art that changes and modifications may be made without departing from the invention, and all such changes and modifications fall within the scope of the invention.

The invention claimed is:

1. A vacuum sealing drainage device for a bleeding wound tissue, the device comprising: a porous foam pad (1) being adapted to contact with the bleeding wound tissue, a drainage piping (2), a sealing film (3), a connector (4), a duct (17), a drainage container (5), a vacuum source (6), a gel membrane (7), at least one outlet pipe (8), and a plurality of support members (9), each of said plurality of support members (9) having a sidewall;
wherein:
said gel membrane (7) is disposed above said porous foam pad (1);
said drainage piping (2) comprises two pipes integrally formed and connected with each other, each pipe of said drainage piping (2) having a cylindrical sidewall and an axis;
said drainage piping (2) is disposed above said porous foam pad (1), and the axes are oriented parallel to a top surface of said porous foam pad (1);
said plurality of support members (9) is hollow and each of said plurality of support members (9) has a plurality of openings (13) disposed on said sidewall;
one end of each of said plurality of support members (9) is disposed in said porous foam pad (1);
the other end of each of said plurality of support members (9) is connected to said drainage piping (2);
one end of said outlet pipe (8) is connected to said cylindrical sidewall;
said sealing film (3) is disposed on the perimeter of said gel membrane (7);
the other end of said outlet pipe (8) is connected to said connector (4), and said connector (4) is connected to said drainage container (5) via said duct;
said drainage piping (2) is disposed between said porous foam pad (1) and said gel membrane (7); and
said one end of said outlet pipe (8) passes through said membrane (7); and
said drainage container (5) is connected to said vacuum source (6) via said duct (17).

2. The vacuum sealing drainage device of claim 1, wherein:
said drainage piping (2) is disposed above the top of said gel membrane (7) and integrally formed with said gel membrane (7).

3. The vacuum sealing drainage device of claim 1, wherein a flow meter (16) is connected to said duct (17) between said outlet pipe (8) and said drainage container (5).

4. The vacuum sealing drainage device of claim 1, wherein said drainage piping (2) and said gel membrane (7) are integrally formed.

5. The vacuum sealing drainage device of claim 3, wherein a pressure sensor (20) is connected to said duct (17);
said pressure sensor (20) is connected to a CPU (21); and
said CPU (21) is connected to said vacuum source (6).

6. The vacuum sealing drainage device of claim 1, wherein said drainage piping (2) comprises two to five pipes disposed parallel to each other.

7. The vacuum sealing drainage device of claim 1, wherein multiple burrs (10) are disposed on said plurality of support members (9).

8. The vacuum sealing drainage device of claim 5, wherein a bacterial filter (18) and an odor filter (19) are disposed between said drainage container (5) and said vacuum source (6).

9. The vacuum sealing drainage device of claim 1, wherein one to five outlet pipes (8) are connected to said drainage piping (2), and said one to five outlet pipes (8) and said drainage piping (2) are integrally formed.

10. The vacuum sealing drainage device of claim 1, wherein a lower end surface of each of said plurality of support members (9) is a concave contour (14).

11. The vacuum sealing drainage device of claim 1, wherein a sealable sample port (15) is disposed on said outlet pipe (8).

12. The vacuum sealing drainage device of claim 1, wherein said outlet pipe (8) is connected to an intersecting area of said top portions.

13. The vacuum sealing drainage device of claim 1, wherein when the device is placed on the wound tissue, said porous foam pad (1) is contacted with the wound tissue and said sealing film (3) is placed on the tissue around the wound tissue, whereby sealing said porous foam pad (1) at the wound tissue.

14. The vacuum sealing drainage device of claim 13, wherein when said porous foam pad (1) is contacted with the wound tissue and when said vacuum source (6) is turned on to apply vacuum, the vacuum is formed successively in said drainage container (5), said duct (17), said connector (4), said outlet pipe (8), each pipe of said drainage piping (2), and said plurality of support members (9), and a negative pressure is transmitted through said support members (9) to said porous foam pad (1) along said pipes of said drainage piping (2); whereby the negative pressure is transmitted along more than one direction to said porous foam pad (1) to create suction.

\* \* \* \* \*